US007904144B2

(12) United States Patent
Causevic et al.

(10) Patent No.: US 7,904,144 B2
(45) Date of Patent: Mar. 8, 2011

(54) METHOD FOR ASSESSING BRAIN FUNCTION AND PORTABLE AUTOMATIC BRAIN FUNCTION ASSESSMENT APPARATUS

(75) Inventors: Elvir Causevic, St. Louis, MO (US); Arthur H. Combs, St. Louis, MO (US)

(73) Assignee: Brainscope Company, Inc., Bethesda, MD (US)

( * ) Notice: Subject to any disclaimer, the term of this patent is extended or adjusted under 35 U.S.C. 154(b) by 1473 days.

(21) Appl. No.: 11/195,001

(22) Filed: Aug. 2, 2005

(65) Prior Publication Data
US 2007/0032737 A1   Feb. 8, 2007

(51) Int. Cl.
*A61B 5/00* (2006.01)
(52) U.S. Cl. .................................................. 600/544
(58) Field of Classification Search .................... None
See application file for complete search history.

(56) References Cited

U.S. PATENT DOCUMENTS

| 3,706,308 | A | 12/1972 | John et al. |
| 4,913,160 | A | 4/1990 | John |
| 5,083,571 | A | 1/1992 | Prichep |
| 5,287,859 | A | 2/1994 | John |
| 5,384,725 | A | 1/1995 | Coifman et al. |
| 5,488,474 | A | 1/1996 | Fateley et al. |
| 5,526,299 | A | 6/1996 | Coifman et al. |
| 6,052,619 | A * | 4/2000 | John ............................ 600/544 |
| 6,360,122 | B1 | 3/2002 | Fischell et al. |
| 6,385,486 | B1 | 5/2002 | John et al. |
| 6,654,623 | B1 | 11/2003 | Kastle |
| 6,658,287 | B1 | 12/2003 | Litt et al. |
| 6,866,639 | B2 | 3/2005 | Causevic et al. |
| 7,054,453 | B2 | 5/2006 | Causevic et al. |
| 7,299,088 | B1 | 11/2007 | Thakor et al. |
| 7,302,064 | B2 | 11/2007 | Causevic et al. |
| 7,373,198 | B2 | 5/2008 | Bibian et al. |
| 7,720,530 | B2 | 5/2010 | Causevic |
| 2002/0039455 | A1 | 4/2002 | Kanamaru et al. |
| 2002/0091335 | A1 | 7/2002 | John et al. |
| 2002/0095194 | A1* | 7/2002 | Charvin et al. ................. 607/55 |
| 2003/0013981 | A1* | 1/2003 | Gevins et al. ................. 600/544 |
| 2003/0181821 | A1 | 9/2003 | Greenwald et al. |
| 2003/0185408 | A1 | 10/2003 | Causevic et al. |
| 2003/0187638 | A1 | 10/2003 | Causevic et al. |
| 2004/0010203 | A1 | 1/2004 | Bibian et al. |
| 2004/0243017 | A1 | 12/2004 | Causevic |

(Continued)

FOREIGN PATENT DOCUMENTS

WO    WO 2005/072459 A2    8/2005

(Continued)

OTHER PUBLICATIONS

Nitish V. Thakor and Shanbao Tong, *Advances in Quantitative Electroencephalogram Analysis Methods*, Annu. Rev. Biomed. Eng., vol. 6, pp. 453-459, Apr. 2, 2004.

(Continued)

*Primary Examiner* — Robert L Nasser
(74) *Attorney, Agent, or Firm* — Finnegan, Henderson, Farabow, Garrett & Dunner, L.L.P.

(57) ABSTRACT

A method and apparatus for performing rapid brain assessment may provide emergency triage to head trauma patients by analyzing a combination of spontaneous and evoked brain potentials. The spontaneous and evoked potentials are analyzed, and the results classified, to present a real-time assessment of a patient's brain, diagnosing any potential abnormalities therein.

34 Claims, 3 Drawing Sheets

U.S. PATENT DOCUMENTS

| | | |
|---|---|---|
| 2004/0267152 A1 | 12/2004 | Pineda |
| 2005/0084014 A1 | 4/2005 | Wang et al. |
| 2005/0113666 A1 | 5/2005 | Bonmassar et al. |
| 2005/0165327 A1 | 7/2005 | Thibault et al. |
| 2006/0217632 A1 | 9/2006 | Causevic et al. |
| 2007/0032737 A1 | 2/2007 | Causevic et al. |
| 2007/0173732 A1 | 7/2007 | Causevic et al. |
| 2008/0208073 A1 | 8/2008 | Causevic |
| 2009/0227889 A2 | 9/2009 | John et al. |

FOREIGN PATENT DOCUMENTS

| | | |
|---|---|---|
| WO | WO 2005/072608 A1 | 8/2005 |
| WO | WO 2006/034024 | 3/2006 |
| WO | WO 2007/016149 A2 | 2/2007 |

OTHER PUBLICATIONS

Jacquin et al., *Adaptive complex wavelet-based filtering of EEG for extraction of evoked potential responses*, Proc. IEEE Int. Conf. Acoust., Speech, and Signal Proc., Philadelphia, PA, Mar. 2005, pp. V:393-396.

Comon, "Independent component analysis, A new concept?," Signal Processing, 36:287-314 (1994).

Delorme et al., "Enhanced detection of artifacts in EEG data using higher-order statistics and independent component analysis," Neurolmage 34:1443-1449 (2007).

Hadjileontiadis et al., "Empirical mode decomposition and fractal dimension filter," IEEE Engineering in Medicine and Biology Magazine, Jan./Feb. 2007, p. 30-39.

Higuchi, "Approach to an Irregular Time Series on the Basis of the Fractal Theory," Physica D 31:277-283 (1988).

Hyvarinen, "Fast and robust fixed-point algorithms for independent component analysis," IEEE Transactions on Neural Networks 10(3):626-634 (1999).

Jung et al., "Removing electroencephalographic artifacts by blind source separation," Psychophysiology 37:163-178 (2000).

Office Action issued May 20, 2010, in corresponding Chinese Application No. 200680032572.1.

Office Action issued May 7, 2010, in correspondence European Application No. 06800351.6.

PCT Search Report and Written Opinion issued by European Patent Office in International Application No. PCT/US2009/040808, mailing date Jul. 31, 2009.

U.S. Appl. No. 12/041,106, filed Mar. 3, 2008.

U.S. Appl. No. 12/059,014, filed Mar. 31, 2008.

Vorobyov et al., "Blind noise reduction for multisensory signals using ICA and subspace filtering, with application to EEG analysis," Biol. Cybern. 86, 293-303 (2002).

PCT International Search Report and the Written Opinion mailed Apr. 22, 2008, in related PCT Application No. PCT/US06/28985.

Jacquin et al., "Optimal Denoising of Brainstem Auditory Evoked Response (BAER) for Automatic Peak Identification and Brainstem Assessment", Proceedings of the 28th IEEE EMBS Annual Int'l Conference, New York, Aug. 30-Sep. 3, 2006, pp. 1723-1726.

PCT International Search Report and the Written Opinion mailed Jul. 2, 2009, in related International Application No. PCT/US2009/035800.

* cited by examiner

METHOD FOR ASSESSING BRAIN FUNCTION AND PORTABLE AUTOMATIC BRAIN FUNCTION ASSESSMENT APPARATUS

FIELD OF THE INVENTION

The invention relates to the field of emergency triage, and specifically, a method and apparatus for performing emergency neurological triage. Moreover, the invention relates to a method and apparatus for assessing brain function.

BACKGROUND OF THE INVENTION

The central nervous system (CNS) and the brain in particular, perform the most complex and essential processes in the human body. Surprisingly, contemporary health care lacks sophisticated tools to objectively assess their function. A patient's mental and neurological status is typically assessed clinically by an interview and a subjective physical exam. The clinical laboratory currently has no capacity to assess brain function or pathology, contributing little more than identification of poisons, toxins, or drugs that may have externally impacted the CNS. Brain imaging studies, such as computed tomography imaging (CT), magnetic resonance imaging (MRI), though widely used and useful, are structural/anatomical tests revealing little or nothing about brain function. In the immediate time of acute brain injury, stroke, or seizure, imaging studies typically reveal no abnormality, even when there is clear and dramatically abnormal brain function. CT and MRI only detect the condition after the morphology or structure of the brain has changed. In some cases it can take from hours to days after the patient is present in an emergency room (ER) before overt changes are evident on the CT or MRI, and before severe neurological pathology is visible. Electrical activity of the brain, however, is affected immediately. New imaging modalities such as functional MRI (fMRI) measure the changes in oxygen saturation in different parts of the brain. Radioisotope imaging such as positron emission tomography (PET) and single photon emission computerized tomography (SPECT) assess chemical changes within the brain as a measurement of function with limited sensitivity and specificity. All of these assessment tools play an important role in selected cases, but they are costly, not universally available, and they do not provide critical information at the early stages of acute care situations. None of the current techniques provides the immediate, actionable information critical to timely intervention, appropriate triage, or the formulation of an appropriate plan of care.

The CNS and brain, of all organs in the human body, are also the most time sensitive and have the least capacity for repair. Currently, emergency room patients with altered mental status, acute neuropathy, or head trauma must undergo costly and time consuming tests to determine an appropriate course of treatment. Unfortunately, in many cases, the clinical condition of patients continue to deteriorate as they wait for equipment to become available or for specialists to interpret tests. The task of the ER physician is to basically establish whether the brain is functioning normally, whether the abnormality is psychiatric or organic in nature, whether an organic abnormality is global or lateralized, and to develop an initial assessment of the diagnostic possibilities. The problem that faces ER physicians is that their resources are quite literally limited to a flashlight and a rubber reflex hammer. Amazingly, all of the physician's decisions concerning the administration of emergency treatment or intervention, including CT scan, spinal tap, additional consultation or discharge are based on the results of this simplistic exam.

Often, ER patients are sent for imaging studies, yet many functional brain abnormalities, such as seizure, are not visible on a CT scan. Some abnormalities which will eventually have anatomical and structural consequences often take time to become visible. This is true for many important conditions such as ischemic stroke, concussion, raised intracranial pressure, and others. Thus, while the location, expense, and limited availability of the CT scan can be problematic, so indeed can the fact that it is a structural as opposed to functional test.

One-third of over 200 physicians surveyed at the American College of Emergency Physicians feel that the combination of a good clinical laboratory, a neurological exam, and a CT scan of the head, is not adequate for the assessment of every patient with altered mental status or neurological dysfunction. Consensus estimates from the CDC NHS database and practicing ER physicians, is that patients requiring a mental status exam represent 15% of the more than 100 million ER visits annually in the U.S., and in some institutions, considerably more.

There are more than 100 million ER visits per year in the US alone (CDC/NCHS) database. In year 2000, more than 13 million of these patients required a formal mental status exam and nearly 5 million had CT scans. This data indicates the need for real-time functional brain state assessment which can be performed in the hospital, in an ambulance, at a sporting event, or any other location where acute neurological evaluation may be necessary.

All of the brain's activity, whether reflexive, automatic, unconscious, or conscious, is electrical in nature. Through a series of electro-chemical reactions, mediated by molecules called neurotransmitters, electrical potentials (voltages) are generated and transmitted throughout the brain, traveling continuously between and among the myriad of neurons. This activity establishes the basic electrical signatures of the electroencephalogram (EEG) and creates identifiable frequencies which have a basis in anatomic structure and function. Understanding these basic rhythms and their significance makes it possible to characterize the EEG as being within or beyond normal limits. At this basic level, the EEG serves as a signature for both normal and abnormal brain function.

The electrical activity of the brain has been studied extensively since the first recordings over 75 years ago, and especially since the advent of computers. "Normal" electrical activity of the brain has been well characterized in hundreds of studies, with a narrow standard deviation. The frequencies of electrical activity of some parts of the brain are the normal response to various stimuli, such as acoustic, visual, or pain, known as "evoked potentials." Evoked potentials (EP) are particular waves that have characteristic shapes, amplitudes and duration of peaks within those wave shapes, and many other features, all of which have well established normative data, generated over decades of research. Normative data for all of the EEG and evoked response waves are remarkably constant across different genders, ages, and ethnicities. Moreover, any variability that does exist is well described and explained.

Neuroscientists have also characterized the EEG signature of various different brain pathologies. Just as an abnormal electrocardiogram (ECG) pattern is a strong indication of a particular heart pathology, an irregular brain wave pattern is a strong indication of a particular brain pathology. A wide array of pathologies have been well characterized: acute and chronic, structural, toxic, metabolic, and even specific diagnoses such as: ischemic stroke, epileptic seizures, concussion, alcohol, and drug overdose, psychiatric conditions, and dementias including Alzheimer's disease. A large body of data, with continuing refinements and contributions, constitutes the field of clinical neurophysiology.

Even though EEG-based neurometric technology is accepted today and a tremendous body of data exists, application in the clinical environment is notably limited. Some of the barriers limiting its adoption include: the cost of EEG equipment, its lack of portability, the need for a technician to administer the test, the time it takes to conduct the test, and the need for expert interpretation of the raw data. More importantly, the technology is neither available nor practical in the acute care setting, especially at the point of care. A complete diagnostic EEG instrument typically costs $80,000, fully equipped. Despite the high costs, the instrument produces essentially raw waveforms which must be carefully interpreted by an expert. Moreover, use of the standard EEG equipment remains extremely cumbersome. It can take 30 minutes or more to apply the required 19 electrodes. Once the patient is prepared for the test, the recording itself can take from 1 to 4 hours. Data is collected and analyzed by an EEG technician, and are then presented to a neurologist for interpretation and clinical assessment. There are some self-standing dedicated neurodiagnostic laboratories which focus strictly on detailed analysis of electrical brain data. Neither the specialized centers, nor the typically large hospital EEG machines are practical for the ER, operating room (OR), intensive care unit (ICU), or any other acute care medicine setting where patients are in the greatest need. Immediate, functional brain state assessment is needed to treat patients with acute neurological injury and disease for the prevention of further damage and disability.

SUMMARY

In accordance with the invention, there is provided a neurological triage apparatus comprising a processor configured to process acquired spontaneous and evoked signals using wavelets.

Also in accordance with the invention, there is provided a method of determining a neurological state of a subject comprising the steps of acquiring spontaneous signals through an electrode set, processing the acquired signals, extracting desired features from the processed signals, and classifying the extracted features into one or more diagnostic categories.

Also in accordance with the invention, there is provided a method of determining a neurological state of a subject comprising the steps of evoking brain response signals using audio, visual, electrical, or other stimulus means, acquiring the evoked signals through an electrode set, processing the acquired signals, extracting desired features from the processed signals, and classifying the extracted features.

Also in accordance with the invention, there is provided a method of determining a neurological state of a subject comprising the steps of acquiring spontaneous and evoked signals through the electrode set, processing the acquired signals, extracting desired features from the processed signals, and classifying the extracted features.

Further in accordance with the invention, there is provided an apparatus for diagnosing the neurological state of a subject, comprising a processor, a memory operatively coupled to the processor, wherein the memory stores one or more operating instructions, a multi-channel input-output interface operatively coupled to the processor, wherein the multi-channel input-output interface is configured to receive external electrical signals through a set of electrodes placed on the subject; and the processor is configured to utilize the one or more operating instructions to perform one or more operations on signals received from the multi-channel input-output interface.

Also in accordance with the invention, there is provided a kit for performing an emergency neurological diagnosis of a patient suffering from an altered mental state, the kit including an apparatus for diagnosing the neurological state of a subject, instructions for using the apparatus, and a portable carrying case for the apparatus.

Also in accordance with the invention, there is provided an apparatus for providing an automatic brain function assessment comprising an electrode set, a processor, wherein the electrode set and the processor are operatively connected through a multi-channel input-output interface, a display operatively connected to the processor, a user interface operatively connected to the processor, and internal memory, wherein the memory contains instructions for providing a real-time assessment of a subject's brain function, and the memory contains instructions for processing signals acquired by the electrode set using wavelet-packet algorithms.

Also in accordance with the invention, there is provided a method for providing a triage assessment of a patient's brain function comprising the steps of measuring the spontaneous brain activity of the patient, stimulating the patient and measuring the evoked brain activity therefrom, processing the spontaneous and evoked brain activity, wherein the processing is performed in real-time using wavelet-packet algorithms, providing a triage assessment of the patient based on the processed brain activity.

Further in accordance with the invention, there is provided a triage apparatus comprising an electrode set, an amplifier operatively connected to the electrode set, a processor operatively connected to the amplifier, wherein the processor is configured to process external signals acquired by the electrode set using wavelets.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiment of the invention and together with the description, serve to explain the principles of the invention.

DESCRIPTION OF THE EMBODIMENTS

Reference will now be made in detail to present embodiments of the invention, an example of which is illustrated in the accompanying drawings. Wherever possible, the same reference numbers will be used throughout the drawings to refer to the same or like parts.

Figure 1:
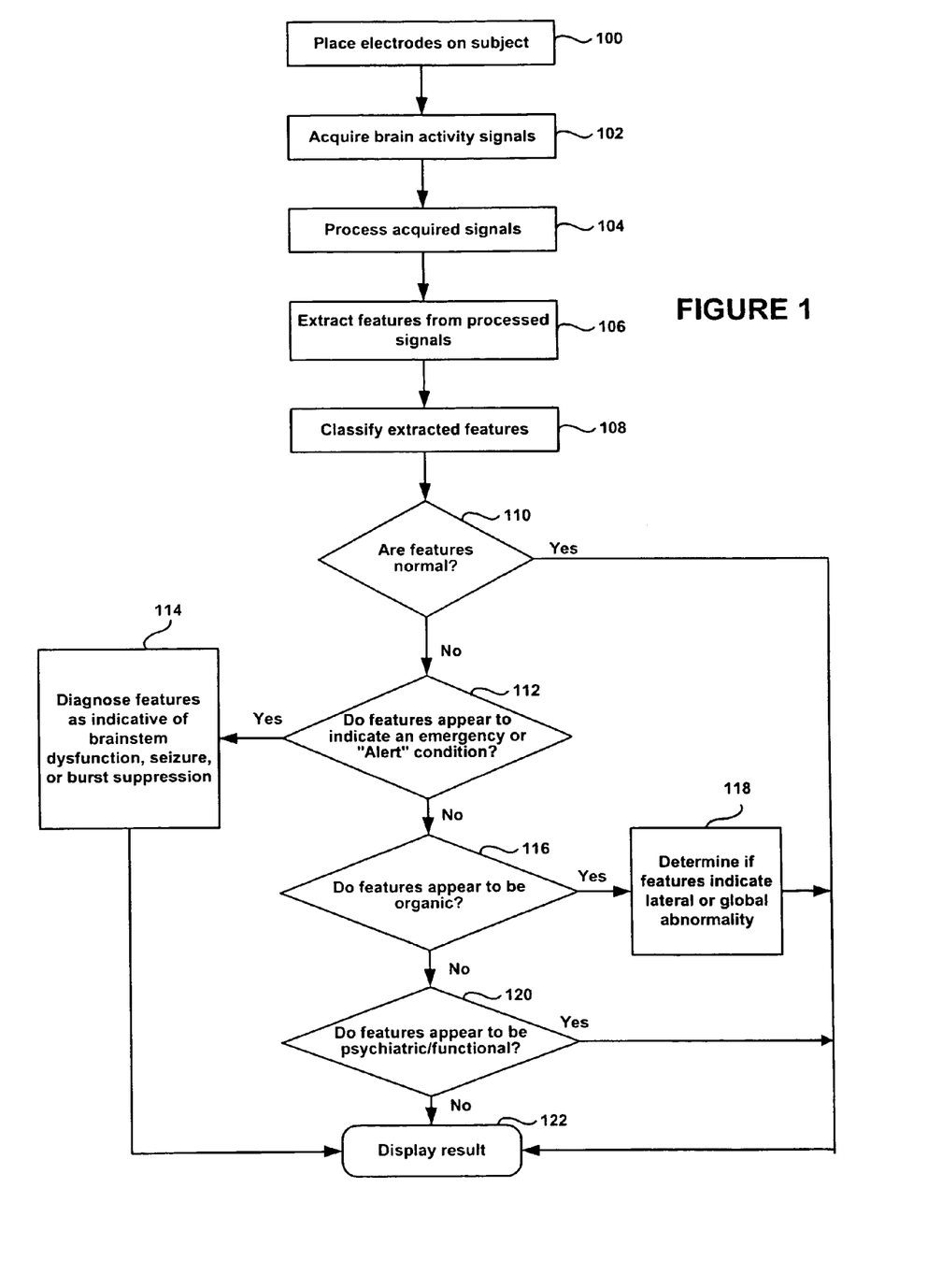
FIG. 1 is a flowchart illustrating the method of assessing the brain state of a subject carried out by an apparatus according to an embodiment consistent with the present invention.

In accordance with embodiments consistent with the present invention, FIG. 1 shows a flowchart illustrating a method for assessing the brain state of a patient. This method may be implemented by an apparatus or device which is manufactured to perform the method given herein. An electrode set is placed on a subject (step 100). Typical electrode sets for acquiring EEG data use at least 19 electrodes. An electrode set consistent with an embodiment of the present invention may comprise a reduced electrode set, with less than 19 electrodes.

The electrodes measure the electrical fields that are produced as a result of the subject's brain activity (step 102). The activity may be spontaneous, evoked or a combination thereof. In an embodiment consistent with the present invention, the spontaneous brain activity is measured and an evoked response is measured. The spontaneous activity may comprise the subject's EEG signals. The evoked response may be obtained by stimulating the subject using visual, physical, auditory, or other stimulation. In an embodiment consistent with the present invention, an auditory stimulus is given to the subject to obtain an Auditory Evoked Potential (AEP). Moreover, the Auditory Evoked Potentials may comprise any of auditory brainstem response (ABR) potentials, auditory mid-latency response (AMLR) potentials, or auditory late response (ALR) potentials, including P100 responses, and P300 responses.

The spontaneous and evoked signals are acquired by the electrode set and are subsequently subjected to a signal processor, wherein artifacts are removed from the signals (step 104). Artifacts that may be removed are a result of such factors as a disconnected electrode, electromyogram (EMG) artifacts resulting from muscular movement, eye movement and other significant artifacts. In one embodiment, the artifacts may be removed by removing discrete artifact sections from the signals. In another embodiment, the artifacts may be removed by subtracting out any artifacts present in the acquired signals.

The artifact-free signals are subjected to further processing to extract statistical signal features (step 106). In one embodiment consistent with the present invention, a quantitative EEG algorithm may be used to extract features. In another embodiment, a wavelet packet algorithm may be used for feature extraction. In a further embodiment, spectral analysis and statistical procedures may be performed to extract features. In yet a further embodiment, diffusion geometric analysis may be performed to extract features. In yet another embodiment, microstate analysis may be performed to extract features. In a further embodiment, wavelet-packet local discriminant basis algorithms may be applied to extract features.

Referring again to FIG. 1, the extracted features are classified according to one or more diagnostic categories, wherein a probability that features extracted from a subject can be classified in one or more diagnostic categories is determined (step 108). According to embodiments consistent with the invention, classifying may be performed by applying discriminant analysis to the extracted features, or by applying wavelet-packets to the extracted features. Regardless of the classifying method used, the classification algorithm first determined if the results are normal (step 110). If the features extracted from the subject's brain waves are normal, then the device will display that the subject's brain activity is normal (step 122). If there is a higher probability that the subject's extracted features are not normal, the device will attempt to classify the extracted features as an emergency or "Alert" condition (step 112). If there is a high probability that the extracted features match features typical of someone in an emergency mental state or an "Alert" condition, the device will attempt to classify the extracted features as either brain-stem dysfunction, active seizure, or burst suppression (step 114). If the device determines that the extracted features have a high probability of being one of the emergency states. the device will display this result so the subject can receive immediate treatment (step 122). If the extracted features do not have a high probability of being an emergency, the device will determine if the abnormality of the extracted features appears to be organic in nature (step 116). If the extracted features are determined to correlate with an extracted feature abnormality that is organic in nature, the device will then attempt to determine if the extracted feature abnormality is lateral or global in nature (step 118), and will display the result (122). The extracted feature abnormalities will be tested to determine if they are psychiatric or "functional" in nature (step 120), and this result will be shown (step 122).

Figure 2:
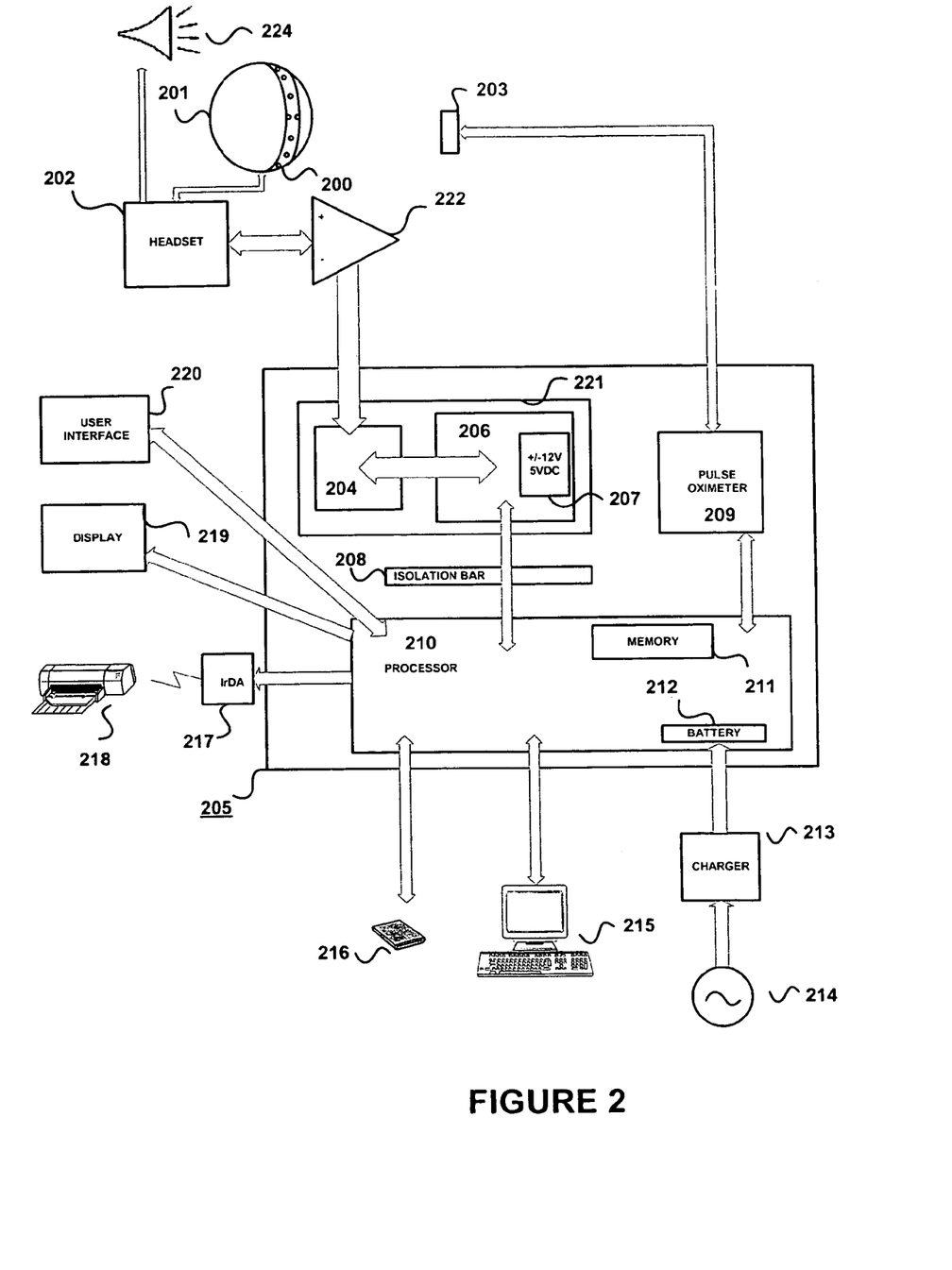
FIG. 2 is a diagram illustrating an apparatus according to an embodiment consistent with the present invention.

FIG. 2 shows an apparatus consistent with an embodiment of the present invention. An electrode set 200 is placed on the head of a subject 201. In an illustrative embodiment, the subject is a human, but the subject can be an animal as well. An electrode set 200 consistent with an embodiment of the present invention may comprise a reduced electrode set, with less than 19 electrodes.

Figure 3:
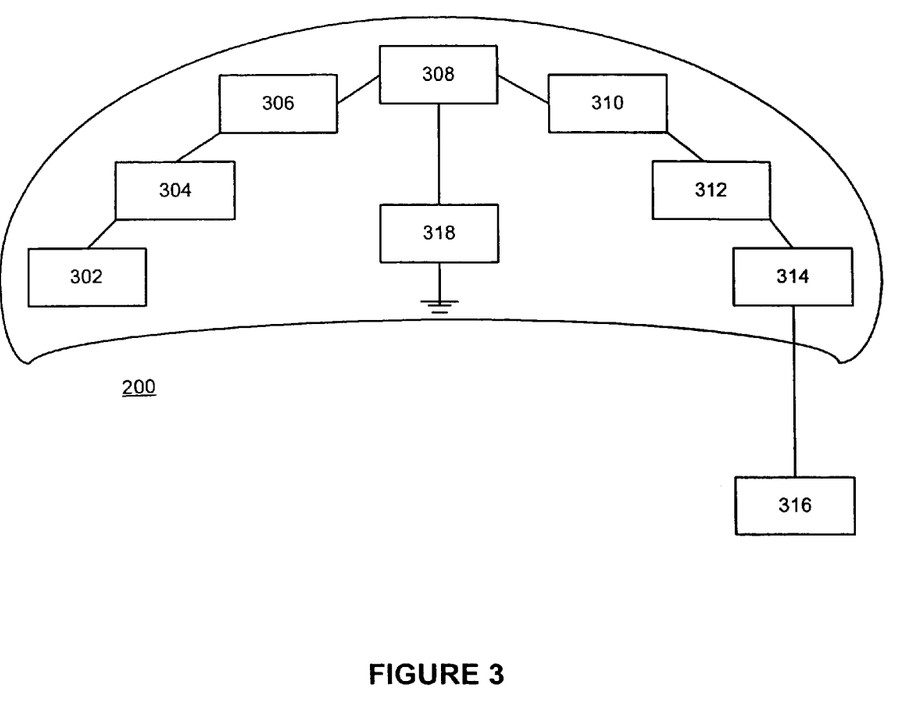
FIG. 3 is a diagram illustrating an electrode set according to an embodiment consistent with the present invention.

FIG. 3 shows an electrode set 200 consistent with an embodiment of the present invention. Electrode set 200 may comprise a plurality of electrodes which may be affixed to the head of a subject 201. In an illustrative embodiment, electrode set 200 comprises nine electrodes that may be affixed to the forehead, shoulder and ear of the subject. This reduced electrode set 200 allows for placement on the forehead, and eliminates the need to place any electrodes over any hair that a subject may have on their head. This further eliminates any conduction problems that arise due to the hair, and also eliminates the need for any hair removal. In an illustrative embodiment, the electrodes may be placed on the right mastoid 302, far right of the forehead 304, near right of the forehead 306, center top of the forehead 308, near left of the forehead 310, far left of the forehead 312, left mastoid 314, and an ECG electrode on the left shoulder 316. Additionally, in an illustrative embodiment, there is an electrode placed on the center of the forehead 318 that is grounded. The electrodes on the right and left mastoids 302, 314 and the center of the forehead 318 may be used in an embodiment wherein an AEP signal is acquired. An illustrative embodiment consistent with the present invention is able to use an electrode set 200 with a reduced number of electrodes because the signal processing algorithms eliminate the need for additional electrodes.

Referring back to FIG. 2, the electrodes measure the electrical fields that are produced as a result of subject's 201 brain activity. The activity may be spontaneous, evoked or a combination thereof. In an embodiment consistent with the present invention, the spontaneous brain activity is measured, for example the EEG of subject 210, and an evoked response is measured. The evoked response may be obtained by stimulating subject 201 using visual, physical, aural or other stimulation. In an embodiment consistent with the present invention, an auditory stimulus is given to subject 201 to obtain an Auditory Evoked Response (AEP). In one embodiment of the present invention, a pulse oximeter 203 is connected to subject 201 to monitor subject's 201 pulse and blood oxygen levels 209.

Electrode headset 202 and pulse oximeter 203 can be connected to a handheld device 205. Electrode headset 202 can be connected to handheld device 205 through a low-voltage preamplifier 222. Low-voltage preamplifier 222 has a high noise tolerance and is designed to amplify the signals that are transmitted to and from electrode headset 202. Handheld device 205 is designed to be able to fit in one's hand. In one embodiment handheld device 205 may have a size of about 115 mm×190 mm×60 mm, and a weight of less than about 600 g. Handheld device 205 has a display 219, which can be an LCD screen, and can further have a touch screen interface and a traditional user interface 220 such as a keyboard. In one embodiment, handheld device 205, electrodes 200 and electrode headset 202 may come in a kit, designed for performing neurological triage of a patient suffering from an altered mental state, wherein the kit includes instructions for using handheld device 205, and comes in a portable carrying case.

Handheld device 205 contains analog and digital hardware on the front end 221, and is controlled through processor 210. In one embodiment, processor 210 is a Texas Instruments OMAP microcontroller/digital signal processor. Front end 221 is separated from processor 210 by isolation barrier 208. Front end 221 acts as a multi-channel input/output interface for the device, further facilitating the bi-directional communication of transmitted and received signals to processor 210. In one embodiment consistent with the present invention, the multi-channel input/output interface is a wireless multi-channel input/output interface.

In an embodiment consistent with the present invention, a command from a user, entered through user interface 220, will begin a test routine. Analog brain waves are acquired through electrode headset 202 and are transmitted through cables to analog front end 204 of handheld device 205. Analog brain waves are then converted to digital signals through an ADC contained in analog front end 204 and transmitted to digital front end 206. Digital front end 206 transmits the digital signals to processor 210 where digital signals are processed in accordance with instructions contained in internal memory 211 of processor 210. In an embodiment consistent with the present invention, the signals are processed to remove noise, processed to extract features, and processed to classify the extracted features. In another embodiment, the instructions contained in internal memory 211 of processor 210 comprise instructions for performing the method illustrated in FIG. 1. Processor 210 may then output results, which may be in real-time, concerning the assessment of subject's 201 brain in accordance with the classification. Outputs may be displayed on LCD screen 219 of handheld device 205, or may be saved to external memory 216, or may be displayed on PC 215 connected to handheld device 205 by serial or universal serial bus connection. In one embodiment, display may display a representation of subject's 201 brain based on the assessment. In another embodiment consistent with the present invention, processor 210 transmits the raw, unprocessed brainwaves to an external memory 216. External memory 216 may be a hard disk drive, an optical disk drive, a floppy disk drive, or a removable, non-volatile memory device. In another embodiment, results are transmitted through serial bus to infrared transmitter 217 which is configured to transmit data wirelessly to printer 218 to wirelessly print results. Handheld device 205 contains an internal rechargeable battery 212 that is able to be charged during use or in between uses through charger 213 connected to a typical AC outlet 214.

In another embodiment, a test routine may require a stimulus to be given to subject 200 to evoke a response. The command to produce a stimulus is transmitted from the processor 210 to digital front end 206, where it is converted to an analog signal by a DAC contained therein. The analog signal is output from the analog front end 204 through the cables and to a stimulus emitter 224 which stimulates subject 201. The stimulus can be auditory, sensory, or visual, or other. In a preferred embodiment, the stimulus is an auditory stimulus given through transmitters that are placed in subject's ear. The stimulus emitter 224 may be an Etymotic Research ER 10D probe with dual speakers and a single microphone in each ear. The evoked signal is acquired by electrode headset 202, and is transmitted along with spontaneous signals to analog front end 204 of handheld device 205, where it is converted to a digital signal and transmitted to digital front end 206. Digital front end 206 transmits the digital acquired signals to processor 210, where evoked response signals are filtered out from spontaneous signals. In an embodiment consistent with the present invention, the evoked response signals are filtered out using an adaptive wavelet based filter. More specifically, internal memory 211 can contain instructions that are executed by the processor 210 which uses a Dual-Tree Complex Wavelet Transform as an invertible transform to adaptively filter evoked signal response signals from spontaneous response signals. The instructions further can contain an implementation of an algorithm carried out by processor 210, wherein a complex wavelet transform is computed for each sub-average, and then the phase variance of each normalized wavelet coefficient $w_{i,j}$ is computed. The magnitude of each wavelet coefficient is selectively scaled according to the phase variance of the coefficients at this location across the sub-averages. The scaling has the form:

$$w_{i,j} = \alpha_{i,j} W_{i,j} \exp(j\theta_{i,j}),$$

where $W_{i,j}$ and $\theta_{i,j}$ are respectively the magnitude and phase of the unprocessed complex $i^{th}$ wavelet coefficient at the $j^{th}$ scale, and where:

$$\alpha_{i,j} = \exp(-0.75(F_{ij}/T_{max})^4,$$

where $F_{ij}$ is the phase variance of coefficient $w_{i,j}$ across the sub-averages. The filtered evoked signal is averaged and an automatic peak detection algorithm is implemented by processor 210 to determine the following peak locations and latencies: Peak 1, Peak 2, and Interpeak 1-5 latency. These values are then compared to normative data contained in internal memory 211 of processor 210.

In an embodiment consistent with the present invention, processing the signals comprises removing noise from the acquired signals, or "de-noising." Internal memory 211 of processor 210 contains instructions for instructing processor 210 to perform an algorithm on acquired signals. In one embodiment, the algorithm utilizes wavelet based signal processing using wavelet transforms. The wavelet transform, a member of the family of Fourier transforms, is a process of decomposing a given signal into a set of orthonormal basis functions called wavelets. In traditional discrete Fourier transform (DFT), a signal is decomposed using complex sinusoids as basis functions, producing a frequency domain representation of the signal. In contrast, a discrete wavelet transform (DWT) uses a family of specifically designed wavelets, or little waves, as basis functions. A family of wavelets is created by dilating the original wavelet function, termed the "mother wavelet." A wavelet transform decomposes the signal in both time and frequency using different dilations of the mother wavelet. With the application of DWT, the one dimensional finite signal x[n] is represented in two-dimensional "wavelet coordinates." Individual levels of signal decomposition are created, called scales. At each scale a set of coefficients is created by computing the inner product of the original signal x[n] with a scaled version of the mother wavelet. The mother wavelet function is designated by $\Psi$, and its dilations are designated by $\Psi(j)$. The position index of a wavelet at scale j is called a translation. The value of the wavelet is completely described by the two dimensional sequence Ψ(j,k), where j is the scale index of the wavelet, and k is the translation index. The DWT is the defined as:

$$C(j,k) = \sum_{n=0}^{N-1} x[n]\Psi_{j,k}[n], \text{ where } \Psi_{j,k}[n] = 2^{\frac{-j}{2}}\Psi(2^{-j}n-k)$$

Coefficients C(j,k) are the wavelet coefficients at different scales j and translations k of the inner product of the wavelet Y(j,k) with the original signal x[n]. In wavelet coordinates, information about both the frequency and the location (time) of the signal energy is preserved. This is a process of noise suppression that utilizes assumptions about smoothness and coherence properties of both the underlying signal and the noise that contaminates it. Similar to filtering in the frequency domain, the wavelet coefficient thresholding algorithm reduces sets of wavelet coefficients in the wavelet domain. This process is based on the assumption that the underlying signal is smooth and coherent, while the noise that is mixed with the signal is rough and incoherent. Smoothness of a signal is a property related to its bandwidth, and is defined in relation to how many times a signal can be differentiated. The degree of smoothness is equal to the number of continuous derivatives that can be calculated. A signal is coherent if its energy is concentrated in both time and frequency domains. An incoherent noise is "spread out," and not concentrated. One measure of coherence is how many wavelet coefficients are required to represent 99% of the signal energy. A time-frequency signal space is completely spanned by wavelet coefficients at all scales and translations. A well-concentrated signal decomposition in an appropriately selected wavelet basis will require very few coefficients to represent 99% of signal energy. However, a completely incoherent noise will require 99% of the coefficients that span the entire space to represent 99% of its energy.

This conventional wavelet de-noising process is a three step process:
1. Wavelet transform the signal to obtain wavelet coefficients at different scales
2. Threshold the coefficients and set to zero any smaller than a threshold δ
3. Perform the inverse wavelet transform to approximate the original signal In the de-noising process, the noise components of the signal are attenuated by selectively setting the wavelet coefficients to zero. De-noising is thus a non-linear operation, because different coefficients are affected differently by the thresholding function. There are many parameters to control in this algorithm: level of wavelet decomposition, threshold selection, using different thresholds at different wavelet coefficients that are kept by a fixed amount.

In accordance with an embodiment of the present invention, the de-noising process involves dividing the acquired signals into discrete intervals, or "frames," and then averaging the frames, and de-noising the averaged frames. The greater amount of frames that are de-noised prior recomposing the signal, the better the results of the de-noising process. Preferably, the frames are combined by using two adjacent frames and calculating their linear average. This method is chosen for its simplicity, computational stability, and well-understood behavior. This dyadic linear average is then de-noised, and a new frame is created. The overall idea is to generate as many permutations of the original arrangement of frames as possible, and keep averaging and de-noising those new combinations of frames. This recombination process is a tree-like process, and may comprise the dual-tree process described above, in which new levels of recombined frames are created. The average and de-noise operation creates frames at level k, which are no longer a linear combination of frames from level k−1.

The many possible algorithms to accomplish this task can be evaluated by different criteria: ease of implementation, computational efficiency, computational stability, etc. For the present invention, ease of implementation is used, because the key aspect of the invention is implementation of different wavelet de-noising techniques and not combinatorics of frame rearrangements. The goal of the preferred embodiment in frame rearranging is to produce enough new frames to obtain acceptable performance.

Processor 210 is further configured to execute instructions contained in internal memory 211 to perform an algorithm for extracting signals from processed signals. In one embodiment, processor 210 executes instructions which performs a quantitative EEG (QEEG) feature extraction algorithm on the processed signals. The algorithm utilizes Fast Fourier Transform (FFT) Analysis is applied to characterize the frequency composition of the processed signals, typically dividing the signals into the traditional frequency bands: delta (1.5-3.5 Hz), theta (3.5-7.5 Hz), alpha (7.5-12.5 Hz), beta (12.5-25 Hz), and gamma (25-50 Hz). Higher EEG frequencies, up to and beyond 1000 Hz may also be used. These features can include characteristics of the processed signals such as absolute and relative power, symmetry, and coherence. In the context of analyzing process brainwaves, absolute power is the average amount of power in each frequency band and in the total frequency spectrum of the processed signals, and is a measure of the strength of the brain's electrical activity. Relative power is the percentage of the total power contributed for a respective electrode and a respective frequency band and is a measure of how brain activity is distributed. Symmetry is the ratio of levels of activity between corresponding regions of the two brain hemispheres in each frequency band and is a measure of the balance of the observed activity. Coherence is the degree of synchronization of electrical events in corresponding regions of the two hemispheres and is a measure of the coordination of the brain activity. These four basic categories of univariate features, resulting from the spectral analysis of the process signals, are believed to characterize independent aspects of brain activity and each is believed to be sensitive to a variety of different clinical conditions and changes of state. A full set of individual and pairwise features is calculated and transformed for Gaussianity using, for example, the log function. Once a Gaussian distribution has been demonstrated and age regression applied, statistical Z transformation is performed. The Z-transform is used to describe the deviations from age expected normal values:

$$Z = \frac{\text{Probability that subject value}}{\text{lies within the normal range}}$$

$$Z = \frac{\text{Subject Value} - \text{Norm for Age}}{\text{Standard Deviation for Age}}$$

The significance of the Z-transform is that it allows measures with different metrics to be combined using the common metric of probability. Using a database of response signals from a large population of subjects believed to be normal, or to have other conditions, the distribution of these response signals is determined for each electrode. In particular, each extracted feature or factor score is converted to a Z-transform score, or factor Z-score which characterizes the probability that the extracted feature value or factor score observed in the subject will conform to a normal value.

Processor 210 is further configured to perform an algorithm wherein the extracted features, or the Z-scores are classified. In one embodiment, these sets of univariate data is subjected to Gaussian normalization in order to improve the accuracy of any subsequent statistical analysis. The Z-scores are given a selected discriminant score. Each discriminant score is a respective weighted combination of a selected subset of Z-scores for monopolar and/or bipolar univariate and multivariate features derived from the processed signals of a subject. The processor 210 executes an algorithm wherein a respective discriminant score is evaluated for each of two or more diagnostic categories multiplying each of several selected Z-scores by a respective coefficient and adding the resulting products. The coefficients typically differ as between diagnostic categories and as between Z-scores. The probability is evaluated that the subject belongs to one of the two or more diagnostic categories through a probability evaluating expression which is a function of the relevant discriminant scores, matching results against limits provided by internal memory 211 for selected brain states.

The diagnostic categories may be indicative of whether a subject is exhibiting normal or abnormal brain function. Moreover, abnormal brain function may be further broken down into diagnostic categories which are indicative of psychiatric or "functional" in nature, organic in nature, either lateral or global, or an emergency or "Alert" condition, which may include seizure, abnormal brainstem response, or burst suppression. Psychiatric or "functional" brain function may further be broken down into specific diagnostic categories indicative of specific types of psychiatric disorders. Similarly, organic lateral and global brain functions may further be broken down into specific diagnostic categories indicative of specific types of lateral and global abnormalities. The ability of the apparatus to determine a probability that subject 201 is experiencing a particular type of abnormal brain function allows a medical professional to act accordingly. For example, should a subject be diagnosed as having a high probability of having a brain function that is indicative of an organic abnormality, the apparatus will further determine whether the brain function has a higher probability of being indicative of a lateral or global abnormality, allowing a medical professional to distinguish between global abnormalities such as concussion, toxicity, encephalitis and the like, and lateral abnormalities such as ischemic and hemorrhagic strokes. This probability that subject 201 belongs to a particular diagnostic category can be displayed on LCD display 219. For example, in the above scenario in which subject 201 is exhibiting an organic, lateral abnormality, LCD display 219 can further display that subject's brain function is 80% indicative of a hemorrhagic stroke, 15% indicative of an ischemic stroke, and 5% of a subdural hematoma. Furthermore, if a subject 201 is diagnosed as having a high probability of suffering from an emergency or "Alert" condition, such as active seizure, a medical professional may be able to provide immediate emergency care to subject 201.

The novel apparatus and method allows the rapid triage assessment of the neurological state of a subject, allowing for immediate diagnosis and care of victims of head injury and neurological maladies. The apparatus may further be packaged in a portable kit with instructions on using the apparatus for performing rapid triage assessment.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining a neurological state of a subject comprising the steps of:
   acquiring spontaneous and evoked signals through an electrode set;
   de-noising the acquired signals;
   extracting features from the de-noised signals using wavelet packet analysis; and
   classifying the extracted features.

2. The method according to claim 1, wherein
   the electrode set comprises less than 19 electrodes.

3. The method according to claim 1, wherein the spontaneous signals comprise:
   electroencephalographic (EEG) signals.

4. The method according to claim 1, wherein the evoked signals comprise:
   auditory evoked potentials (AEP).

5. The method according to claim 4, wherein the auditory evoked potentials comprise at least one of:
   auditory brainstem response (ABR) potentials, auditory mid-latency response (AMLR) potentials, or auditory late response (ALR) potentials, including P100 responses and P300 responses.

6. The method according to claim 1, wherein the step of de-noising the signals comprises:
   de-noising the acquired signals using signal transformation and non-linear processing.

7. The method according to claim 6, wherein the step of de-noising the signals further comprises:
   filtering the signals using a dual-tree complex wavelet transform of the acquired signals.

8. The method of according to claim 1, wherein the step of de-noising the signals comprises:
   removing artifacts from the acquired signal by identifying artifact sections in the acquired signals and subtracting the identified artifact sections.

9. The method according to claim 1, wherein the step of extracting features comprises:
   performing spectral analysis and statistical procedures on the de-noised signals, and extracting features.

10. The method according to claim 9, wherein applying spectral analysis comprises:
    applying a Fast Fourier Transform (FFT) to the de-noised signals, dividing the signals into frequency bands.

11. The method according to claim 1, wherein
    the extracted features include absolute and relative power, symmetry and coherence.

12. The method according to claim 1, wherein the step of extracting features further comprises:
    applying Fast Fourier Transform (FFT) analysis on the de-noised signals to extract features.

13. The method according to claim 1, wherein the step of classifying comprises:
    applying discriminant analysis to the extracted features to classify the extracted features into one or more diagnostic categories.

14. The method according to claim 1, further comprising the step of:
    determining a neurological state of the subject based on the classification.

15. The method according to claim 14, wherein the step of determining further comprises:
    determining if the neurological state is normal or abnormal.

16. The method according to claim 15, further comprising:
    determining if an abnormal neurological state is psychiatric or "functional" in nature, organic in nature, or an emergency or "Alert" condition.

17. The method according to claim 16, wherein neurological states that constitute an emergency condition include seizure, abnormal brainstem response, or burst suppression.

18. The method according to claim 15, further comprising:
    determining if an abnormal neurological state that is organic in nature is global or lateral.

19. The method according to claim 1, further comprising:
    graphically displaying the determination;
    graphically displaying representations of the brain based on the determination;
    storing data related to the determination.

20. The method according to claim 1, wherein the step of extracting features comprises:
    performing a high-speed quantitative electroencephalograph (qEEG) algorithm on the de-noised signals to extract features.

21. A method for providing a triage assessment of a patient's brain function comprising the steps of:
    measuring, using electrodes, the spontaneous brain activity of the patient;
    stimulating the patient and measuring the evoked brain activity therefrom;
    processing, using a processor coupled to a memory having instructions for processing stored therein, the spontaneous and evoked brain activity, wherein
        the processing is performed in real-time using a wavelet-packet algorithm to extract signal features;
        providing a triage assessment of the patient based on the processed brain activity.

22. The method according to claim 21, wherein
    the steps of processing and providing an assessment are performed by a portable hand-held device.

23. A method of determining a neurological state of a subject comprising the steps of:
    acquiring spontaneous and evoked signals through an electrode set;
    processing the spontaneous and evoked signals using a processor coupled to a memory having instructions for processing stored therein, wherein processing the spontaneous and evoked signals further comprises the steps of:
    de-noising the acquired signals;
    extracting features from the de-noised signals;
    classifying the extracted features; and
    determining a neurological state of the subject based on the classification, wherein determining the neurological state further comprises the steps of:
        determining if the neurological state is normal or abnormal; and
        determining if an abnormal neurological state that is organic in nature is global or lateral.

24. The method according to claim 23, wherein the spontaneous signals comprise electroencephalographic (EEG) signals and the evoked signals comprise auditory evoked potentials (AEP).

25. The method according to claim 23, wherein the step of extracting features from the denoised signal comprises using a wavelet packet transform algorithm.

26. The method of claim 23, wherein said classifying step further comprises non-linear classification.

27. A method of determining a neurological state of a subject comprising the steps of:
    acquiring brain electrical signals using a set of neurological electrodes;
    processing the acquired brain electrical signals using a processor coupled to a memory having instructions for processing stored therein, wherein processing the acquired brain electrical signals further comprises the steps of:
    de-noising the acquired signals;
    extracting features from the de-noised signals;
    classifying the extracted features into a first set of diagnostic categories using discriminant analysis, wherein the first set of diagnostic categories are indicative of whether the subject has a normal or an abnormal neurological state; and
    classifying an abnormal brain state into a second set of diagnostic categories using discriminant analysis, wherein the second set of diagnostic categories are indicative of whether the subject's abnormal neurological state is psychiatric or "functional" in nature, organic in nature, or an emergency or "Alert" condition.

28. The method according to claim 27, wherein an emergency or "Alert" condition is further classified into diagnostic categories indicative of seizure, abnormal brainstem response, or burst suppression.

29. The method according to claim 27, wherein an organic condition is further classified into diagnostic categories indicative of a global or lateral abnormality.

30. The method according to claim 27, wherein electrical brain signals comprise spontaneous brain signals.

31. The method according to claim 27, wherein the electrical brain signals comprise evoked potentials.

32. The method according to claim 27, wherein the electrical brain signals comprise spontaneous brain signals and evoked potentials.

33. The method according to claim 27, wherein the extracted features comprise quantitative non-linear features.

34. The method of claim 27, wherein said classifying step further comprises non-linear classification.

* * * * *